United States Patent [19]

Dotson, Jr. et al.

[11] 4,262,149

[45] Apr. 14, 1981

[54] PROCESS FOR SEPARATING ALKANOLS FROM AQUEOUS CALCIUM CHLORIDE

[75] Inventors: Anderson O. Dotson, Jr., Somerset, N.J.; Francis T. Wadsworth, Monroe, La.

[73] Assignee: Columbian Chemicals Company, Tulsa, Okla.

[21] Appl. No.: 142,272

[22] Filed: Apr. 21, 1980

[51] Int. Cl.$^3$ .................... C07C 29/88; C07C 29/86; C07C 41/06; C07C 41/38
[52] U.S. Cl. .................................. 568/697; 568/699; 568/918; 568/923
[58] Field of Search ............... 568/918, 923, 697, 699

[56] References Cited

U.S. PATENT DOCUMENTS

| | | | |
|---|---|---|---|
| 1,442,520 | 1/1923 | Buc | 568/699 |
| 2,179,991 | 11/1939 | Bright et al. | 568/923 |
| 2,595,544 | 5/1952 | Rodman | 568/918 |
| 3,455,664 | 7/1969 | Rosscup et al. | 568/918 |
| 3,940,450 | 2/1976 | Lee | 568/699 |

FOREIGN PATENT DOCUMENTS 7807035  1/1979  Netherlands .............................. 568/697

*Primary Examiner*—Joseph E. Evans
*Attorney, Agent, or Firm*—Patricia J. Hogan

[57] ABSTRACT

A $C_1$–$C_2$ alkanol is separated from aqueous calcium chloride by adding a $C_4$ or $C_5$ hydrocarbon feed comprising an isoolefin to an aqueous solution of a calcium chloride-alkanol complex wherein the alkanol is methanol or ethanol at a temperature of about 80°–120° C. and a pressure of about 20–180 psig to provide an upper phase comprising the hydrocarbon feed and alkanol and a lower phase comprising aqueous calcium chloride. The invention is particularly useful as a step in a process for preparing and purifying methyl t-butyl ether by (1) reacting an excess of methanol with isobutylene or a $C_4$ hydrocarbon stream containing isobutylene to form a crude reaction product comprising methyl t-butyl ether and excess methanol, (2) intimately mixing the crude reaction product with aqueous calcium chloride to complex the methanol and separate it from the ether, and (3) adding the hydrocarbon stream to extract the methanol from the aqueous calcium chloride-methanol complex solution.

12 Claims, No Drawings

PROCESS FOR SEPARATING ALKANOLS FROM AQUEOUS CALCIUM CHLORIDE

BACKGROUND OF THE INVENTION

1. Field of the Invention

This invention relates to a process for separating alkanols from aqueous calcium chloride. More particularly, it relates to a process for back extracting alkanols from aqueous solutions of calcium chloride-alkanol complexes formed in separating alkanols from alkyl t-alkyl ethers.

2. Description of the Prior Art

As shown in Netherlands published application No. 7,807,035 (Snam Progetti); U.S. Pat. Nos. 3,940,450 (Lee) and 4,148,695 (Lee et al.); John C. Davis et al., "MTBE bandwagon," CHEMICAL ENGINEERING, May 21, 1979, pp. 91–93; and Stephen C. Stinson, "New plants, processes set for octane booster," CHEMICAL & ENGINEERING NEWS, June 25, 1979, pp. 35 and 36, it is known that alkyl t-alkyl ethers can be prepared by reacting an isoolefin with an alkanol in the presence of an ion exchange resin. Such reactions have general interest, although the greatest current interest is in the reaction of isobutylene with methanol to form methyl t-butyl ether. Methyl t-butyl ether has utility as an additive for improving the octane rating of gasoline.

In the reactions of isoolefins with alkanols, it is preferred to use an excess of alkanol in order to minimize the formation of by-products. However, the use of an excess of alkanol results in contaminating the ether product with a difficultly removable impurity. The alkanol forms an azeotrope with the ether and therefore cannot be separated therefrom by simple atmospheric distillation.

It is frequently desirable to separate the alkanol from the ether. It is also desirable to separate the alkanol from any unreacted hydrocarbons in the crude reaction product, since alkanols are poisons for alkylation catalysts and, if not removed, would make the unreacted hydrocarbons unsuitable for use in alkylation units. Thus, since atmospheric distillation canot be used, it is conventional to remove the alkanol by pressure distillation. This method of removing the alkanol is costly in terms of energy requirements and capital investment.

An economical and efficient process for separating alkanols from alkyl t-alkyl ethers and unreacted hydrocarbons is disclosed in copending application Ser. No. 069,210, filed Aug. 23, 1979, in the names of Anderson O. Dotson, Jr., and Francis T. Wadsworth. In the preferred process of that application, aqueous calcium chloride is intimately admixed with an ether-alkanol mixture to form a calcium chloride-alkanol complex which is easily separable from the ether; and, when it is desired to reuse the calcium chloride and alkanol, the complex is separated into reusable components by stripping the alkanol at about 100° C. This process has decided advantages over conventional methods of separating alkanols from ethers, but it would be desirable to find an even more economical way of separating the alkanol from aqueous calcium chloride when reuse of the alkanol and calcium chloride components of the complex is wanted.

SUMMARY OF THE INVENTION

An object of this invention is to provide an economical process for separating $C_1$–$C_2$ alkanols from aqueous calcium chloride.

Another object is to provide such a process wherein an aqueous calcium chloride-alkanol complex is separated into components suitable for use in the preparation and purification of alkyl t-alkyl ethers.

These and other objects are attained by adding a $C_4$ or $C_5$ hydrocarbon feed comprising an isoolefin to an aqueous solution of a calcium chloride-alkanol complex wherein the alkanol is methanol or ethanol at a temperature of about 80°–120° C. and a pressure of about 20–180 psig to provide an upper liquid phase comprising the hydrocarbon feed and alkanol and a lower liquid phase comprising aqueous calcium chloride.

DESCRIPTION OF THE PREFERRED EMBODIMENTS

Calcium Chloride-Alkanol Complex

The calcium chloride-alkanol complex that is treated in accordance with the invention may be any aqueous solution of a calcium chloride-alkanol complex wherein the alkanol is methanol or ethanol. However, in commercial operations, it will ordinarily be a complex formed by intimately mixing (1) a mixture comprising methanol or ethanol and an ether corresponding to the formula R-O-R', wherein R is a methyl or ethyl group and R' is a t-butyl or t-amyl group, with (2) an aqueous solution containing at least 0.25 mol of calcium chloride per mol of alkanol to form a calcium chloride-alkanol complex; and it will frequently contain excess, uncomplexed calcium chloride.

Alkanol-ether mixtures from which the complexes of the invention may be derived may be any mixtures comprising the alkanols and ethers just mentioned, since the proportionation of the components is not critical, and the mixtures may consist only of the alkanols and ethers or may have other components. However, most commonly, such a mixture is the crude reaction product, i.e., the total reaction mixture, resulting from the reaction of an excess of methanol or ethanol with isobutylene or isoamylene to form an alkyl t-alkyl ether. Such reactions are well known and include processes wherein the alkanol is reacted with pure isoolefin and processes wherein the alkanol is reacted with a steam-cracker or catalytic-cracker $C_4$ or $C_5$ hydrocarbon stream containing the isoolefin and other hydrocarbons primarily having the same number of carbon atoms. A typical process utilizes a $C_4$ hydrocarbon stream containing 25–55% by weight of isobutylene, a methanol/isobutylene mol ratio of 1.7, an ion exchange resin as a catalyst, a reaction temperature of about 90°–100° C., and a pressure of about 280 psig, although other reactants and other conditions are also utilizable when desired.

As is also well known, the crude reaction products resulting from such processes are generally mixtures of the desired ether, unreacted alkanol, unreacted hydrocarbon, and small amounts of by-products, although by-product formation is minimized by the use of an excess of the alkanol. For example, in the typical process mentioned above, the crude reaction product typically contains methyl t-butyl ether, methanol, isobutylene, n-butane, isobutane, cis-butene-2, trans-butene-2, butene-1, and small amounts of t-butyl alcohol and diisobutylene. On the other hand, when pure isoolefin is used as a starting material, isoolefin is the only unreacted hydrocarbon in the crude reaction product.

In deriving the complexes of the invention from such alkanol-ether mixtures, the alkanol-ether mixture is intimately mixed with an aqueous solution containing at least 0.25, preferably about 0.25-10, and most preferably about 0.5-5, mols of calcium chloride per mol of alkanol and generally having a concentration of at least 30%, preferably about 35-45%, and most preferably about 40-44% by weight. The intimate admixture results in the formation of an aqueous calcium chloride-alkanol complex which, together with any excess calcium chloride, can be easily separated from the other components because the cessation of agitation inherently results in the separation of the mixture into (a) an upper phase comprising the ether and any unreacted hydrocarbon and by-products and (b) a lower phase comprising the calcium chloride-alkanol complex and any excess calcium chloride in water. The aqueous phase can then simply be withdrawn from the bottom of the vessel in which the mixture was formed and is then suitable for use in the practice of the present invention.

As taught in the aforementioned copending application Ser. No. 069,210, the teachings of which are incorporated herein by reference, the formation of an aqueous calcium chloride-alkanol complex is sometimes part of a process which comprises (1) charging the crude reaction product of an isoolefin-alkanol reaction to a separator, (2) intimately mixing the crude reaction product in the separator with aqueous calcium chloride to form a calcium chloride-alkanol complex, (3) withdrawing the ether and any unreacted hydrocarbon and by-products from the separator as overhead, (4) when appropriate, separating the ether, unreacted hydrocarbon, and by-products by conventional techniques, (5) withdrawing the aqueous calcium chloride-alkanol complex and any excess calcium chloride from the separator as bottoms, (6) separating the alkanol from the aqueous calcium chloride, (7) recycling the separated alkanol to the reactor, and (8) recycling the separated aqueous calcium chloride to the separator. The use of the present technique of separating an alkanol from aqueous calcium chloride to accomplish step 6 in this process is a preferred embodiment of the present invention.

Hydrocarbon Feed

The hydrocarbon feed of the invention may be any $C_4$ or $C_5$ hydrocarbon feed comprising an isoolefin. Thus, it may be pure, or at least substantially pure, isobutylene or isoamylene or a $C_4$ or $C_5$ hydrocarbon stream, e.g., a steam-cracker or catalytic-cracker stream, containing the isoolefin and other hydrocarbons primarily having the same number of carbon atoms. In a preferred embodiment of the invention, when the process of the invention is a step in the overall process described in the preceding paragraph, at least a portion of the hydrocarbon feed is the unreacted hydrocarbon portion of the overhead withdrawn from the separator in step 3.

The amount of hydrocarbon feed employed in the practice of the invention is not critical. Since the calcium chloride does not have to be completely free of complexed alkanol to make it utilizable for complexing more alkanol, it is not necessary to accomplish complete separation of the calcium chloride and alkanol. However, it is usually desirable to separate at least about 50% of the alkanol from the aqueous calcium chloride, and excellent results may be achieved by adding at least about 1.3 parts by weight of hydrocarbon feed per part of complexed alkanol until at least about 80%, preferably at least about 90% of the alkanol has been recovered from the aqueous solution. Frequently the total weight of hydrocarbon feed employed is in the range of about 1.3-3 times the weight of complexed alkanol.

Process Conditions

As mentioned above, the process of the invention is conducted at a temperature of about 80°-120° C. and a pressure of about 20-180 psig to provide an upper phase comprising the hydrocarbon feed and alkanol and a lower phase comprising aqueous calcium chloride. The phases may then be separated by conventional techniques. When the inventive process is a step in the above-described process for preparing and purifying an alkyl t-alkyl ether by (1) reacting an alkanol with an isoolefin to form the ether, (2) charging the crude reaction product to a separator wherein it is contacted with aqueous calcium chloride to separate the ether and unreacted hydrocarbon from the alkanol, (3) withdrawing the resultant aqueous calcium chloride-alkanol layer, and (4) separating the alkanol therefrom, the entire upper phase formed in the inventive process, i.e., the hydrocarbon-alkanol phase, is ordinarily recycled to the reactor, where it may be combined with any necessary make-up alkanol and isobutylene; and the lower phase, i.e., the aqueous calcium chloride phase, is ordinarily recycled to the separator, where it may be supplemented by any additional aqueous calcium chloride required.

The invention is particularly advantageous in that it provides an alkanol-aqueous calcium chloride separation technique that is more economical than any known technique for accomplishing the separation and which permits alkyl t-alkyl ethers to be prepared and purified with less energy consumption than the cnventional processes require. It is notable that ether syntheses using the process of the invention require less heat input for the alkanol-isoolefin reaction because the recycled hydrocarbon-alkanol phase is already at an elevated temperature when it enters the reactor.

The following examples are given to illustrate the invention and are not intended as a limitation thereof. Unless otherwise specified, quantities mentioned in the examples are quantities by weight.

EXAMPLE I

Charge 72 parts of 44% aqueous calcium chloride and 36.5 parts of methanol to a suitable autoclave to form a calcium chloride-methanol complex. Seal the autoclave, heat its contents to 100° C., and add 100 parts of a $C_4$ hydrocarbon stream containing isobutylene through a dip tube which falls below the surface of the aqueous solution. Pass the hydrocarbon stream through the reactor by adding a portion thereof, stopping the feed, allowing the pressure to reach 150 psig, venting methanol and $C_4$ hydrocarbons from the upper phase formed in the process, collecting the vented vapors in a dry ice/alcohol cold trap, and repeating the procedure until all of the hydrocarbon stream has passed through the reactor. The total addition time is 30 minutes. Cool the autoclave to ambient temperature and weigh both the material collected in the cold trap and the aqueous solution in the reactor. The process results in the recovery of 90% of the methanol. The aqueous solution contains all of the original water and calcium chloride and 10% of the methanol.

EXAMPLE II

Charge a mixture of 221 parts of methanol and 450 parts of a $C_4$ hydrocarbon stream containing 50.8% isobutylene to a tubular reactor packed with an acidic ion exchange resin. React the ingredients at 100° C. to form a reaction mixture comprising methyl t-butyl ether, excess methanol, and unreacted hydrocarbons. Withdraw this reaction mixture from the bottom of the reactor and charge it to a separator equipped with mixing baffles and agitators and having (1) a bottom entry port for introduction of the reactor effluent, (2) an entry port in the upper side, (3) a top exit port, and (4) a bottom exit port.

While operating the agitators, charge 900 parts of 44% aqueous calcium chloride through the upper entry port to provide countercurrent admixture of the reactor effluent and aqueous solution at 35° C. and formation of a $CaCl_2.4CH_3OH$ complex. Withdraw the ether and unreacted hydrocarbons through the top exit port and separate them. Drain an aqueous calcium chloride/calcium chloride-methanol complex mixture through the bottom exit port.

Charge the aqueous mixture withdrawn from the bottom of the separator to a suitable autoclave, seal the autoclave, and heat its contents to 100° C. Continuously pass 48 parts of a $C_4$ hydrocarbon stream containing 50.8% isobutylene through the autoclave while maintaining a pressure of 150 psig to form an upper phase consisting of methanol and $C_4$ hydrocarbons and a lower phase comprising aqueous calcium chloride. Continuously withdraw the upper phase and recycle it to the tubular reactor through a closed conduit. Continuously withdraw the aqueous calcium chloride phase and recycle it to the separator.

The process leads to the isolation of methyl t-butyl ether and $C_4$ hydrocarbons that are substantially free of methanol, and it separates about 92% of the methanol from the calcium chloride-methanol complex to provide methanol and aqueous calcium chloride streams suitable for use in subsequent reactions.

EXAMPLE III

Repeat Example II except for replacing the hydrocarbon feed to the autoclave with the unreacted hydrocarbon portion of the overhead withdrawn from the separator. Similar resuts are observed.

Similar results are also observed when the examples are repeated except that the ingredients are replaced with ingredients taught to be their equivalents in the specification.

We claim:

1. A process which comprises adding a $C_4$ or $C_5$ hydrocarbon feed comprising an isoolefin to an aqueous solution of a calcium chloride-alkanol complex wherein the alkanol is methanol or ethanol at a temperature of about 80°-120° C. and a pressure of about 20-180 psig to provide an upper phase comprising the hydrocarbon feed and alkanol and a lower phase comprising aqueous calcium chloride.

2. The process of claim 1 wherein the hydrocarbon feed is substantially pure isobutylene.

3. The process of claim 1 wherein the hydrocarbon feed is a $C_4$ hydrocarbon stream containing isobutylene.

4. The process of claim 1 wherein the alkanol is methanol.

5. The process of claim 1 wherein the weight of hydrocarbon feed added to the aqueous solution is at least about 1.3 times the weight of alkanol in the calcium chloride-alkanol complex.

6. The process of claim 1 wherein the hydrocarbon feed is added until at least about 50% of the alkanol has been recovered from the aqueous solution.

7. The process of claim 6 wherein the hydrocarbon feed is added until at least about 80% of the alkanol has been recovered from the aqueous solution.

8. The process of claim 6 wherein the hydrocarbon feed is added until at least about 90% of the alkanol has been recovered from the aqueous solution.

9. A process which comprises (1) adding at least about 1.3 parts by weight of a $C_4$ hydrocarbon stream containing isobutylene to an amount of an aqueous solution of a calcium chloride-methanol complex containing one part by weight of complexed methanol at a temperature of about 80°-120° C. and a pressure of about 20-180 psig to provide an upper phase comprising the hydrocarbon feed and at least about 90% of the methanol and a lower phase comprising aqueous calcium chloride and up to about 10% of the methanol and (2) separating the upper phase from the lower phase.

10. In a process for preparing an ether by:
(A) reacting an excess of a $C_1$-$C_2$ alkanol with an isoolefin containing 4 or 5 carbon atoms to form a crude reaction product comprising a mixture of (1) an ether corresponding to the formula R-O-R', wherein R is a methyl or ethyl group and R' is a t-butyl or t-amyl group, (2) unreacted alkanol, and (3) unreacted hydrocarbon,
(B) charging the crude reaction product to a separator,
(C) intimately mixing the crude reaction product in the separator with an aqueous solution containing at least 0.25 mol of calcium chloride per mol of unreacted alkanol to form a calcium chloride-alkanol complex and provide a two-phase mixture consisting of an upper layer comprising the ether and unreacted hydrocarbon and a lower layer comprising the aqueous calcium chloride-alkanol complex,
(D) withdrawing the ether and unreacted hydrocarbon from the separator as overhead,
(E) withdrawing the aqueous calcium chloride-alkanol complex from the separator as bottoms,
(F) separating the alkanol from the aqueous calcium chloride,
(G) recycling the separated alkanol to the reactor, and
(H) recycling the separated aqueous calcium chloride to the separator, the improvement which comprises:
(a) separating the alkanol from the aqueous calcium chloride by adding a $C_4$ or $C_5$ hydrocarbon feed comprising an isoolefin to the bottoms of step E at a temperature of about 80°-120° C. and a pressure of about 20-180 psig to provide an upper phase comprising the hydrocarbon feed and alkanol and a lower phase comprising aqueous calcium chloride and
(b) recycling the entire upper phase containing the separated alkanol to the reactor.

11. The process of claim 10 wherein (1) the crude reaction product is the product obtained by reacting an excess of methanol with a $C_4$ hydrocarbon stream containing isobutylene and (2) the hydrocarbon feed is a $C_4$ hydrocarbon stream containing isobutylene.

12. The process of claim 11 wherein the hydrocarbon feed comprises the unreacted hydrocarbon portion of the overhead of step D.

* * * * *